United States Patent [19]
Nielsen

[11] B 3,991,104
[45] Nov. 9, 1976

[54] TRISULFOSUCCINIC ACID

[75] Inventor: Donald R. Nielsen, Corpus Christi, Tex.

[73] Assignee: PPG Industries, Inc., Pittsburgh, Pa.

[22] Filed: Aug. 5, 1974

[21] Appl. No.: 494,669

[44] Published under the second Trial Voluntary Protest Program on February 3, 1976 as document No. B 494,669.

[52] U.S. Cl. .................. 260/513 R; 260/513 B; 252/156; 252/535; 252/537; 252/538; 252/554; 252/556
[51] Int. Cl.² .................................. C07C 143/04
[58] Field of Search.......... 260/513 R, 513 B, 513 T

[56] References Cited
UNITED STATES PATENTS

| | | | |
|---|---|---|---|
| 3,138,632 | 6/1964 | Scotti et al. | 260/513 B |
| 3,533,944 | 10/1970 | Yuan | 260/513 B |
| 3,798,183 | 3/1974 | Bruson et al. | 260/513 B |

OTHER PUBLICATIONS
Beilsteins, Handbuch der Organisch Chem. Band 4, Vierte Auflage, p. 13 (1922).

*Primary Examiner*—James O. Thomas, Jr.
*Assistant Examiner*—Nicky Chan
*Attorney, Agent, or Firm*—Roger S. Benjamin

[57] ABSTRACT

Disclosed is trisulfosuccinic acid and salts thereof described by the formula:

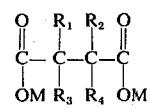

where one of $R_1$, $R_2$, $R_3$ or $R_4$ is hydrogen and the remainder are $SO_3M$; and where M may be the same or different cation selected from hydrogen or an alkali metal. These compounds may be prepared by aqueous liquid phase reaction of a dihalomaleic anhydride, alkali metal hydroxide and an alkali metal sulfite and are useful as detergent builders.

3 Claims, 1 Drawing Figure

O = STPP
△ = PENTASODIUM TRISULFOSUCCINATE

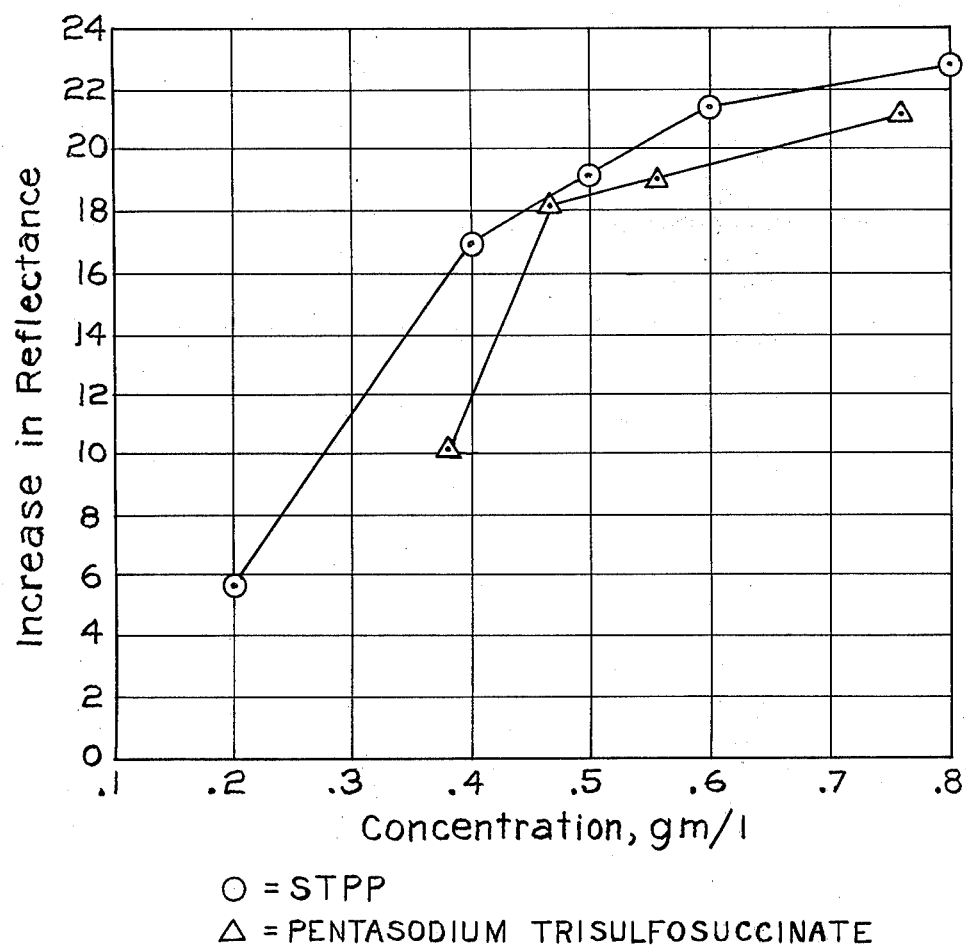

TRISULFOSUCCINIC ACID

BACKGROUND OF THE INVENTION

Builders are additives used to improve the detergency levels of surface active agents. The mechanism by which builders act to improve detergency may involve precipitation or sequestration of hardness causing ions, aiding emulsification, or stabilizing suspensions. Until recently, phosphorous-based compounds, particularly sodium tripolyphosphate (STPP), found extensive use in detergent formulations. Recognition that phosphorouscontaining ingredients which are cycled to water sources contribute to eutrophication has made it desirable to develop non-phosphorous-containing detergent formulations.

THE INVENTION

The present invention relates to novel compositions, notably trisulfosuccinic acid and alkali metal salts thereof described by the formula:

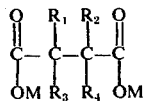
(I)

where one of $R_1$, $R_2$, $R_3$ or $R_4$ is hydrogen and the remainder are $SO_3M$; and where M may be the same or different cation selected from hydrogen or an alkali metal, i.e., sodium, potassium, lithium or ammonium. Those compounds in which M is but one alkali metal, notably sodium, are typified by pentasodium trisulfosuccinate.

DETAILED DESCRIPTION OF THE INVENTION

The compounds of the present invention may be prepared by the reaction of a dihalomaleic anhydride, such as dichloromaleic anhydride together with sodium hydroxide or other alkali metal hydroxide and sodium sulfite or other alkali metal sulfite in aqueous solution. The synthesis is represented by the following equations:

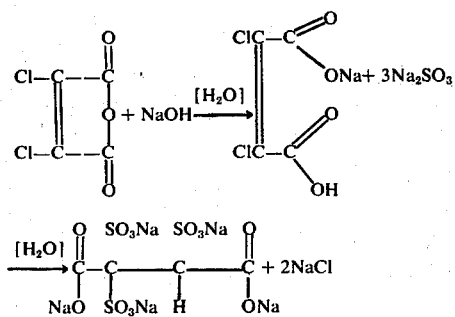
(II)

The reaction is normally carried out utilizing the reagents in stoichiometric proportions. Dihalomaleic acids or alkali metal salts thereof may be employed in lieu of the anhydride as illustrated by reactions III and IV.

Reaction of a dihalomaleic acid with an alkali metal hydroxide and an alkali metal sulfite:

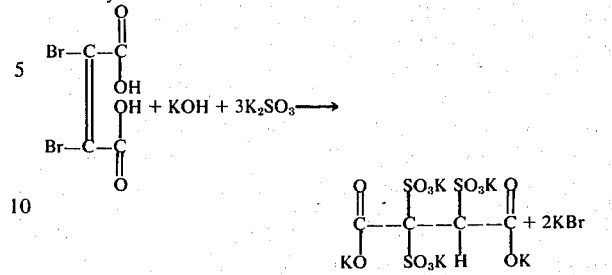
(III)

Reaction of a di-alkali metal salt of a dihalomaleic acid with an alkali metal sulfite and an alkali metal acid sulfite:

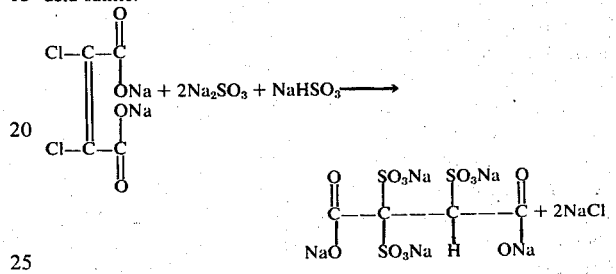
(IV)

Suitable dihalomaleic starting materials include the dichloro, dibromo and diiodo maleic anhydrides, or acids, or alkali metal salts thereof, the dichloro derivatives being preferred. In effecting the reaction, the dichloro reagent is typically charged to a reactor. Then the hydroxide is added along with the alkali metal sulfite. Alternatively, the hydroxide may be added to form the intermediate and the sulfite added thereafter. One or more ingredients may be added in excess of that required to effect reaction if desired. The identity of "M" in the formula (I) will depend on the alkali metal cation of the hydroxide and sulfite. Suitable alkali metal hydroxides or sulfites include NaOH, $NH_4OH$, KOH, LiOH, $Na_2SO_3$, $K_2SO_3$ and $Li_2SO_3$. As used herein, the words, "alkali metal," includes ammonium.

The alkali metal cation of both the hydroxide and the sulfite will be the same when the desired trisulfosuccinate is to have only the same alkali metal cation such as pentasodium trisulfosuccinate, pentapotassium trisulfosuccinate and pentaammonium trisulfosuccinate. Use of reagents with different cations results in a mixture of trisulfosuccinates having different alkali metal cations, as for example, mono-sodium, tetrapotassium, trisulfosuccinate; mono-potassium, tetra-sodium trisulfosuccinate; and ammonium, tetra-potassium trisulfosuccinate.

The free acid, trisulfosuccinic acid, may be prepared by reacting the alkali metal salt of trisulfosuccinic acid with a proton donor such as an ion-exchange resin in hydrogen form or a strong acid such as HCl or $H_2SO_4$ under conditions where alkali metal salts of the equilibrium reaction are removed. When the trisulfosuccinic acid is subsequently employed in a media made alkaline by alkali metal bases, it will be reconverted to an alkali metal salt form.

Reaction is carried out in liquid aqueous media. The reaction temperature may range from the boiling point of the aqueous solution downward, provided the reaction medium is liquid. Temperatures from 80°C. to 150°C. are preferred. If desired, the reaction may be conducted at superatmospheric pressures to attain temperatures above 100°C. in a liquid aqueous environment.

In the normal course of preparing the alkali metal salts of the trisulfosuccinic acid according to the reactions typified by II, III, and IV, the reaction product may contain impurities in the form of other sulfosuccinic acids or unreacted reagents. Such impurities are not detrimental to the role of trisulfosuccinic acid as a detergent builder and may be included in a detergent composition. If desired, trisulfosuccinic acid may be separated from accompanying salts which are either reactants or reaction products (e.g., alkali metal hydroxides, or chlorides). One means of removing salts which are either unused reactants or reaction products (e.g., NaOH, $Na_2SO_3$, NaCl) from the aqueous solution of trisulfosuccinic acid or its alkali metal derivatives is by contacting the solution with an ion-exchange resin in hydrogen form and thereafter evaporating the solution at reduced pressure (e.g., removal of contained HCl or $SO_2$).

The builders of this invention may be used with synthetic surfactants of the anionic, cationic or non-ionic types. Surfactants useful in the practice of this invention are described in the article, *Surface-Active Agents*, Volume 13, pages 513–536 of the *Encyclopedia of Chemical Technology*, edited by R. E. Kirk and D. F. Othmer, Interscience Publishers, New York (1954). In particular, the following surfactants have utility in combination with trisulfosuccinic acid and its salts:

ANIONIC SURFACTANTS

Anionic surfactants which are suitable include various salts of alkyl sulfonates, phosphate esters alcohol sulfates, sulfated ethoxylated alkyl phenols, sulfated fatty acid esters, sulfated and sulfonated oils and fatty acids, dodecyl and tridecyl benzene sulfonates, petroleum sulfonates and taurates.

In addition, alkyl, aryl or alkyl aryl phosphates in either the free acid or alkali metal salt form can be used. Other anionic detergents include the alkyl alkali metal sulfosuccinates, the modified coconut diethanolamides, the amine salts of alkyl benzene sulfonic acids, high molecular weight alkyl aryl sulfonates and alkali metal salts thereof.

Additional anionic surfactants useful in the present invention are sodium isopropylnaphthalene sulfonate, the dioctyl ester of sodium sulfosuccinic acid, sulfated castor oil, sodium alkylaryl sulfonate, sodium ethoxylated sulfosuccinate, sodium lauryl ether sulfates, sodium lauryl sulfates, sodium 2-ethylhexyl sulfate, tridecyl sodium sulfate, and sodium N-methyl-N-oleyltaurate.

CATIONIC SURFACTANTS

Those cationic surfactants which can be employed include the quaternary ammonium salts such as aliphatic dimethyl benzyl ammonium chlorides where the hydrocarbon chain is lauryl, cetyl, stearyl and oleyl.

Dilauryl dimethyl ammonium chloride is also useful. Cyclic amines such as pyridine, picoline and butadiene may form the basis for useful quaternary salts such as, for example, lauryl pyridinium chloride. Those compositions which have been designed to combine germicidal power with detergency such as the polyalkylnaphthalene methyl pyridinium chlorides and the substituted benzyl:2,4-dichlorobenzyl dimethyl lauryl ammonium chlorides can be used. Other useful cationic detergents include the ethanolated alkylguanidine amine complexes, cetyl dimethylbenzyl ammonium chloride, cetyl trimethyl ammonium bromide, myristyl diethyl amine oxide and alkyl dimethyl amine oxide.

NON-IONIC SURFACTANTS

Non-ionic surfactants useful in the process include alkanolamides; ethoxylated alcohols, amides, amines and fatty acids; glycerol esters and sorbitan derivatives.

Additional specific non-ionic surfactants useful in the process of the instant invention include sorbitan monoleate, and coconut diethanolamide, fatty alcohol polyglycol ether carboxylic acids, fatty alkylolamine condensates, coco amido propyl dimethyl amine oxide, and condensates of fatty alcohols with ethylene oxide.

The optimum ratio of builder to surfactant will change depending on variables such as soil levels, concentration of hardness causing ions and pH. In general, a range of 0.1 to 10.0 parts by weight of tri-sulfosuccinic acid or its salts are used per part by weight of surfactant to form an effective cleaning composition. The trisulfosuccinic acid base builder may be used in any order of addition with the surfactant. For example, the trisulfosuccinic acid may be added to an aqueous washing media containing surfactant, or both components may be added together. The concentration of builder is typically 0.01 to 0.2 parts by weight per 100 parts by weight of aqueous washing medium.

In addition to the surfactant and trisulfosuccinic acid builder, the cleaning composition may contain such additional conventional additives as soil removing agents (e.g., sodium silicate), anti-redeposition agents (e.g., carboxymethylcellulose), as well as optical brighteners, bleaching agents, perfumes, etc. The cleaning composition may also contain inert fillers such as sodium sulfate or sodium chloride. It is also within the scope of this invention to use the trisulfosuccinic acid builders in combination with other known builders. The builders of this invention may be used together with alkali metal polyphosphate builders should it be desired to reduce the quantity of phosphorous in a cleaning composition.

The following examples illustrate the preparation of trisulfosuccinic acid and its salts as well as its use as a builder in detergent compositions. All percentages in the Examples are percent by weight unless otherwise indicated.

EXAMPLE I

This example illustrates the preparation of trisulfosuccinic acid and its salts. A solution of 79.4 grams (0.63 mole) of sodium sulfite, 8.0 grams (0.2 mole) of NaOH and 33.4 grams (0.2 mole) of dichloromaleic anhydride in 300 milliliter $H_2O$ was allowed to reflux at atmospheric pressure in a 500 milliliter flask equipped with a water-cooled condenser for 22 hours. At the end of this time, titration with standardized iodine solution indicated that 0.56 mole of sodium sulfite had been consumed. The reaction mixture was evaporated at approximately 2 millimeters Hg pressure at about 20°C. to give 122.6 grams of product which contained 16.5 percent sodium chloride, as determined by a Volhard titration, 3.3 percent $Na_2SO_4$, as determined by precipitation as $BaSO_4$ and 1.6 percent $Na_2SO_3$, as determined by titration with standardized iodine solution.

A portion of the product was passed through a column of hydrogen form cation-exchange resin (Dowex 50W-X8 — a styrene-divinylbenzene base ion-exchange resin, product of Dow Chemical Co.) and the column effluent was evaporated at reduced pressure (2 millimeter Hg) at room temperature. The residue, a syrup which solidified after standing for several weeks, had an acid number of 9.8 (theor. for trisulfosuccinic acid, 14.0). Elemental analysis showed 9.41 percent C, 3.88 percent H and 24.36 percent S (calc. for trisulfosuccinic acid 13.4 percent C, 1.68 percent H, 26.8 percent S). Addition of $BaCl_2$ to 2.40 grams gave 3.02 grams Ba salt (theor. wt. 4.67 grams). The product contained 43.7 percent Ba, 5.99 percent C and 1.23 percent H (calc. for Ba trisulfosuccinate tetrahydrate 44.5 percent Ba, 6.25 percent C and 1.17 percent H). These analytical results confirm the formation of a product containing 70 percent trisulfosuccinic acid and 30 percent $H_2O$.

EXAMPLE II

Soil cloth designated EMPA 101, purchased from Test Fabrics, Inc. was cut into four inch square swatches for use in the following example. Two such cloth swatches in soiled condition were placed into individual wash containers of an Atlas Launder-Ometer along with 300 milliliters of wash solution and 20 one-quarter inch steel balls as agitation aids.

The wash solution consisted of 0.3 grams per liter of anionic surfactant (80 percent sodium-n-dodecylbenzene sulfonate; trademarked Sulframin 85, Witco Chemical Co.), 0.105 grams per liter sodium silicate, 0.015 grams per liter carboxymethyl cellulose along with 150 parts per million hardness calculated as $CaCO_3$, with a Ca:Mg mole ratio of 3:2. The pentasodium trisulfosuccinate was added as the reaction mixture of Example I. The trisulfosuccinic acid was added in the form of the 70 percent trisulfosuccinic acid syrup of Example I. The detergent builders, trisulfosuccinic acid and STPP, were added to different wash solutions to form a comparison test (see Table 1 and drawing).

The cloth swatches were allowed to remain in the Launder-Ometer containers with agitation for 15 minutes at 50°C. The swatches were removed and rinsed with distilled water. They were then hand rung and ironed dry with care taken to iron only the side of the swatch opposite the side upon which the reflectance measurements were to be taken. Reflectance readings were taken both before and after the wash cycle with an automated Hunter Reflectometer using a green filter, the results of which are found in Table 1.

The increase in reflectances between the unwashed and washed swatches at various concentrations of trisulfosuccinic acid and STPP are graphically compared in the drawing. Phosphorous-free sulfosuccinic acid and its salts possess ecological advantages in their use as replacement for present day detergent builders such as STPP. The drawing illustrates that pentasodium trisulfosuccinate approaches the effectivenss of STPP in an aqueous media simulating commercial formulations under typical washing conditions.

While the present invention has been described by reference to certain embodiments, it is not intended that the invention be construed as limited to such specific details except insofar as such details appear in the claims.

I claim:

1. Trisulfosuccinic acid or its salt described by the formula:

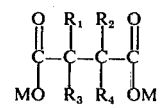

where one of $R_1$, $R_2$, $R_3$ or $R_4$ is hydrogen and the remainder are $SO_3M$; and where M may be the same or different cation selected from hydrogen or an alkali metal.

2. Trisulfosuccinic acid.

3. Pentasodium trisulfosuccinate.

TABLE 1

Effect of Builders on Soil Removal from EMPA 101 Test Cloth

| Builder Used with Wash Solution of Example II | Conc. g/l | Reflectance Units (Avg.) | | |
|---|---|---|---|---|
| | | After | Before | Increase |
| STPP | 0.2[a] | 25.0 ± 1.1 | 19.4 ± 0.4 | 5.6 ± 1.2 |
| | 0.4 | 35.9 ± 0.4 | 19.2 ± 0.2 | 16.7 ± 0.4 |
| | 0.5 | 38.3 ± 0.8 | 19.2 ± 0.7 | 19.1 ± 1.1 |
| | 0.6 | 40.4 ± 0.6 | 18.9 ± 0.2 | 21.5 ± 0.6 |
| | 0.8 | 42.1 ± 0.5 | 19.3 ± 0.2 | 22.8 ± 0.5 |
| Pentasodium Trisulfosuccinate | .37 | 29.6 ± 0.6 | 19.1 ± 0.6 | 10.5 ± 0.8 |
| | .47 | 37.2 ± 0.7 | 19.1 ± 0.5 | 18.1 ± 0.9 |
| | .56 | 38.0 ± 1.8 | 19.0 ± 0.5 | 19.0 ± 1.9 |
| | .76 | 40.0 ± 0.4 | 19.4 ± 0.4 | 20.6 ± 0.6 |
| Trisulfosuccinic Acid[b] | .28 | 29.1 ± 0.6 | 19.1 ± 0.5 | 10.0 ± 0.7 |
| | .56 | 39.8 ± 0.4 | 19.5 ± 0.3 | 20.3 ± 0.5 |

[a]This solution was cloudy. All others were clear.
[b]The acid form converts to a sodium salt in the alkaline environment of Example II.